United States Patent [19]

Razumov et al.

[11] 4,162,311
[45] Jul. 24, 1979

[54] MEDICINAL PREPARATION WITH PRONOUNCED VEGETOTROPIC AND ANTIEPILEPTIC EFFECT FOR TREATING PSYCHONEUROTIC DISORDERS

[76] Inventors: Alexandr I. Razumov, ulitsa Ak. Gubkina, 17, kv. 34; Irina V. Zaikonnikova, ulitsa Chekhova, 4b, kv. 1; Vladimir S. Chudnovsky, ulitsa Dekabristov, 189, kv. 59; Galina F. Rzhevskaya, ulitsa Stepana Khalturina, 16, kv. 72; Raisa I. Tarasova, ulitsa 8 Marta, 2, kv. 28; Nina A. Bljukherova, ulitsa Ershova, 20, kv. 57; Rimma L. Yafarova, ulitsa Zhdanova, 66, kv. 62, all of Kazan; Grigory Y. Avrutsky, ulitsa 3 Parkovaya, 38, korpus 1 kv. 109, Moscow; Vladimir G. Belikov, ulitsa Krasnoarmeiskaya, 11a, kv. 15, Pyatigorsk; Anatoly V. Litvinenko, ulitsa Pionerskaya, 14, kv. 37, Kazan, all of U.S.S.R.

[21] Appl. No.: 848,583

[22] Filed: Nov. 4, 1977

[51] Int. Cl.² ............................................. A61K 31/66
[52] U.S. Cl. ................................................. 424/211
[58] Field of Search ........................................ 424/211

[56] References Cited
PUBLICATIONS

Chem. Abst., 67, 100208(a) (1967).
Chem. Abst., 73, 118641(v) (1970).

Primary Examiner—Stanley J. Friedman
Attorney, Agent, or Firm—Steinberg & Blake

[57] ABSTRACT

The proposed medicinal preparation comprises a filler and an active principle which is hydrazide of diphenylphosphinylacetic acid of the formula:

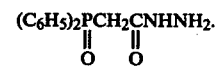

The filler may be starch and calcium stearate.

The preparation is administered in the form of pills containing about 83 percent by weight of the active principle.

The preparation of this invention is advantageous over the existing preparations used for treating neurotic and psychic disorders with pronounced vegetative disturbances in that it has a greater regulating effect on vegetative disturbances. The proposed preparation is the most effective for treating temporal lobe epilepsy with psychosensory, psychomotor, emotional and vegetative paroxysms.

The preparation is well endured by patients. It produces no complications, nor side effects and can be used over prolonged periods of time for treating both young and old patients.

3 Claims, No Drawings

MEDICINAL PREPARATION WITH PRONOUNCED VEGETOTROPIC AND ANTIEPILEPTIC EFFECT FOR TREATING PSYCHONEUROTIC DISORDERS

FIELD OF THE INVENTION

The present invention relates to medicine and, more particularly, to medicinal preparations with a pronounced vegetotropic and antiepileptic effect, used for treating psychoneurotic disorders.

BACKGROUND OF THE INVENTION

Synthetized drugs for treating psychoneurotic disorders accompanied by paroxysmal and persistent vegetovascular disturbances and the temporal lobe epilepsy syndrome began to be commonly used in the 1950's and 60's. Such preparations include, first of all, tranquilizers, for example, diazepam, chlorodiazepoxide, nitrazepam, tazepam and others. The active principle in these preparations is a compound of the benzodiazepine derivatives. Diazepam and chlorodiazepoxide exhibit the most pronounced vegetotropic and antiepileptic effect, but even these preparations are not effective enough for treating the above-mentioned disorders. For example, in the case of the diencephalic syndrome with pronounced vegetative crises the use of the said tranquilizers, which feature vegetotropic activity, only tends to mitigate the manifestations of the disease, without reducing the frequency of vegetative crises. As a result, the treatment is ineffective and the state of the patients remains unchanged. Likewise, in the case of temporal lobe epilepsy with psychosensory, psychomotor and vegetative crises the use of tranquilizers of the benzodiazepine derivatives only brings about a temporal slackening of paroxysmal activity, without preventing further development of psychic disorders. This results in attempts to treat temporal lobe epilepsy surgically, which in itself is indicative of drug therapy limitations. Besides, both diazepam and chlorodiazepoxide manifest a relaxing effect and produce sluggishness when taken over prolonged periods of time. Attempts to treat the aforesaid diseases with magnesia, vitamins, calcium ion ophoresis, diphenylhydramine hydrochloride, novocain, and vegetable sedatives (belladonna, Valeriana officinalis) produce, as a rule, only a limited and short-lived effect. Meanwhile, there are very many cases of organic lesions of the brain which affect the vegetative functions and are psychosomatic diseases; the drug therapy in the treatment of such cases continues to be a vital problem.

OBJECT OF THE INVENTION

It is an object of the present invention to provide a new medicinal preparation for treating psychoneurotic disorders, which would be marked by an intensified vegetotropic and antiepileptic effect and considerable therapeutic activity.

The foregoing object is attained by providing a medicinal preparation with a pronounced vegetotropic and antiepileptic effect, intended for treating psychoneurotic disorders and comprising an active principle and a filler, wherein the active principle is hydrazide of diphenylphospinylacetic acid of the formula:

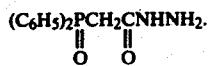

The filler may be starch and calcium stearate.

The proposed drug is prepared in the form of pills, wherein the active principle content is 83.3 percent by weight.

Literature does not mention any attempts to use phosphorus-containing compounds, including the medicinal preparation of the present invention, which do not possess anticholinesterase properties, as neurotropic and psychotropic drugs.

Being a relatively weak tranquilizer, the proposed preparation mainly acts upon the vegetative regulation centers in the limbic and diencephalic structures of the brain, wherein the epileptogenic focus is found in cases of temporal lobe epilepsy.

Hydrazide of diphenylphosphenylacetic acid is a bitter-tasting odorless white powder. It is chemically stable both in the form of powder and solution, and its shelf life may be longer than two years.

Experiments on animals revealed a pronounced sedative effect of the proposed preparation. In tolerance doses, beginning with ⅛ DMT, it causes depression in mice and rats without bringing the animals to what is known as the "on-side" position. Intra-abdominal administration of the preparation in an amount of ⅛ DMT one hour before the experiment affects the orientating reaction in mice.

When interacting with narcotics and soporifics, hydrazide of diphenylphsophinylacetic acid potentiates hexenal, barbamil, urethane and chloral hydrate and exhibits the properties of a true Brodie potentiator. A dose as low as 1/5 DMT potentiates barbamil. Hexenal introduced during the period of action of hydrazide of diphenylphosphinylacetic acid 2 and 22 hours after the administration induces sleep of equal duration, which indicates that the preparation does not suppress the monoaminooxidaze activity.

In a dose of 30 mg/kg (1/7 DMT) and 60 mg/kg (166 DMT) hydrazide of diphenylphosphinylacetic acid has no effect on the body temperature of mice; in a dose of 200 mg/kg (DMT), it produces a hypothermal effect 1.5 and 3 hours after the administration, bringing down the body temperature 4.3° and 3.4° C., respectively. Hydrazide of diphenylphosphenylacetic acid also intensifies the hypothermal effect of the central adrenolytic drug, i.e. aminazine (chlorpromazine). This is another proof of the fact that hydrazide of diphenylphospinylacetic acid possesses tranquilizing properties.

The action of hydrazide of diphenylphosphinylacetic acid is related to its central adrenolytic effect. The preparation of this invention prevents death of 60 percent of mice subjected to a lethal dose of cocaine. It also counters group toxicity of phenamine (amphetamine), in which case it prevents death of 30 to 60 percent of mice. In a broad range of doses (from 10 mg/kg to 400 mg/kg) it causes a statistically reliable reduction in the duration of phenamine stereotypy in rats; when taken in great doses, it prevents the advent of phenamine sereotypy.

Experiments on separated intenstines and studies of the effects of hydrazide of diphenylphosphenylacetic acid on the blood pressure and respiration of rabbits revealed that the proposed preparation has no peripheral adrenolytic effect.

Studies of the functions of separated intestines of rabbits, rats and guinea pigs subjected to the effects of hydrazide of diphenylphosphinylacetic acid in combination with acetylcholine, barium chloride, histamine and serotonin revealed that the preparation of the present invention prevents the action of serotonin on a separated rat's intestine. It was also established that the proposed preparation decreases the serotonin content in brain tissue of mice. The antiserotin effect of hydrazide of diphenylphosphinylacetic acid also accounts for its synergism with the effects of nibuphin, another organophosphorous compound possessing antiserotin properties.

Like reserpine, hydrazide of diphenylphosphinylacetic acid increases the sensitivity of mice to the convulsant effects of corasole and caffeine. However, in contrast to hydrazine antidepressants which inhibit monoamine oxidase, hydrazide of diphenylphosphenylacetic acid has no cumulative effect; it does not intensify the toxicity of apomorphine in mice, nor does it affect the duration of apomorphine stereotypy.

Thus with regard to its effect on phenamine (amphetamine) stereotypy in mice, hydrazide of diphenylphosphinylacetic acid exhibits the properties of a central adrenolytic; as regards its effect on apomorphine stereotypy, it exhibits the properties of a cholinolytic. The latter is further corroborated by the ability of the proposed preparation to relieve nicotine-induced convulsions in mice, whereby the survival rate is increased 50 percent. Hydrazine of diphenylphosphinylacetic acid has no M-cholinolytic effect; it does not mitigate arecoline tremor in mice, nor does it affect its duration.

Thus experiments on animals show that hydrazide of diphenylphosphinylacetic acid acts as a depressant, which is due to its adrenolytic and, possibly, N-cholinolytic effects. As regards the effects of the proposed preparation on convulsions induced in animals in the course of an experiment, the mechanism of action appears to be more complicated. The preparation does not prevent convulsions caused by corasole, strychnine, and electroconvulsion therapy. However, administered in a dose of 20 to 100 mg/kg, it prevents or reduces the frequency of epileptic seizures in rabbits, caused by microinjections of penicillin into the hippocamp.

In experiments on mice, the preparation produces an analgetic effect beginning with a dose of ¼ DMT. Administered in a dose of ½ DMT, hydrazide of diphenylphosphinylacetic acid produced an analgetic effect during three hours after the administration. DMT produced more than five hours of analgesia. In a dose of ½ DMT hydrazide of diphenylphosphinylacetic acid intensified the analgetic effect of analginum; in a dose of ¼ DMT it intensified the analgetic effect of morphine.

Clinical studies of 32 cases of vegetovascular dystonia showed that a course of treatment had normalized the functions of the sympathoadrenal and hypothalamohypophysioadrenal systems. A pronounced normalization of the excretion of adrenalin and 17-oxycorticosteroids with urine was observed, as well as a tendenecy towards a normalized extraction of norepinephrine.

The localization of brain structures that are the most sensitive to hydrazide of diphenylphosphinylacetic acid was studied on rabbits having electrodes permanently implanted in different parts of the cerebral cortex and subcortical formations. It was established that in a dose of 100 to 200 mg/kg, the proposed preparation reduces the electrical activity in hippocamp and amygdaloid nuclei.

Hydrazide of diphenylphosphinylacetic acid has no local irritant effect and a limited toxicity (when injected intravenously, $LD_{50}$ amounts to 293 mg/kg). Intramuscular administration of the preparation to rabbits in no way affected the animals's behavior even in doses of 50 mg/kg. Prolonged treatment with hydrazide of diphenylphosphinylacetic acid (intraperitoneal administration to mice in a dose of 35 mg/kg - $1/9 LD_{50}$, and intramuscular administration to rabbits in a dose of 50 mg/kg) brings about no changes in the blood and internal organs of animals, which could be detected in the course of anatomical and histological examination.

The effects of the proposed preparation were studied in clinical conditions on 157 patients suffering from different neurotic and psychic disorders, including neuroses (neurasthenia, hysteric neurosis, obsessional neurosis), reeactive depression, involutional depression, alcoholism with symptoms of acute alcoholic abstinence, temporal lobe epilepsy, and the diencephalic (hypothalamic) syndrome with vegetovascular crises.

The preparation was administered in the form of pills containing 0.25 to 0.5 g of the active principle. The average daily dose amounted to 1.0 to 3.0 g (doses of 0.5 to 1 g were given 2 or 3 times a day irrespective of the mealtimes). The treatment is continued over a period from one to six and even eight weeks; in the case of temporal lobe epilepsy it takes 3 to 5 months.

According to clinical investigation data, the proposed preparation exhibits a tranquilizing effect, although it is less pronounced than in the case of diazepam and chlorodiazepoxide. The proposed preparation acts as a light night sleep compeller in cases of neuroses, accelerates the onset of sleep and reduces the number of times the patient awakes at night. Clinical investigation also shows good tolerance of the preparation and the absence to a marked relaxation effect typical of the derivatives of benzodiazepin; no side effects or complications are caused by the proposed preparation.

The basic advantage of the preparation according to the invention resides in its marked effect on vegetative regulation disturbances and its antiepileptic action.

Of 20 cases of hypothalamic syndrome accompanied by sympathoadrenal crises, a marked improvement was observed in 5 cases, when vegetative crises ceased and the patients' working capacity was restored. In 12 cases the number and intensity of fits were reduced and general improvement was observed. Earlier, all the patients had been repeatedly admitted to neurological hospitals where they were subjected to different forms of treatment, including drug therapy with the use of tranquilizers of the benzodiazepin derivatives. The effect of such treatment was quite moderate and unstable and was only manifest in a reduced number of fits and a slight improvement of the general state of the patients.

The proposed preparation also proved to be therapeutically effective in cases of neurasthenia with marked symptoms of vegetovascular dystonia. Of 11 patients, 8 showed a significant improvement as soon as at the end of the first week of treatment, as well as a reduced number or even complete eliminationn of vegetovascular crises accompanied by tachycardia, dyspnea, a rising arterial pressure, phobias and anxieties.

Of 30 alcoholics in the state of acute alcoholic abstinence accompanied by pronounced vegetovascular disturbances and phobias, 20 showed a considerable improvement during the first two days of the treatment; of 30 control patients who were given placebo, only 10 showed some improvement. On the whole, the proposed preparation reduced the period of abstinence 2- to 3-fold.

Good results were also obtained in treating 18 cases of temporal lobe epilepsy with predominant psychosensory, psychomotor, vegetative and emotional fits. For a number of years, all the patients had been given anticonvulsants and tranquilizers which were derivatives of benzodiazepin. In most of these cases conventional treatment had been ineffective. The proposed preparation brought about a dramatic change: in 14 cases the attacks either ceased completely or their frequency was reduced by more than half. The state of the patients improved, dysphorias were better endured, and the patients' behavior became more controlled. Electroencephalography revealed a reduction in the paroxysmal activity and normalization of recordings.

Prolonged use of the proposed preparation (over periods of 8 to 12 weeks) does not change the morphological and biochemical composition of the blood; nor are there any changes that could be detected by electrocardiography.

The above clinical data indicates that the proposed preparation is highly effective in treating neurotic and psychic disorders accompanied by vegetovascular disturbances and epileptic fits without convulsions, and that it is superior in this respect to the known drugs. The preparation of this invention can be administered over prolonged periods of time because it produces no side effects or complications, has low toxicity and is not habit-forming. The proposed preparation can be used for treating both young and old patients, as well as those having concomitant diseases of internal organs. The only contraindication is the gastric ulcer with a tendency to frequency exacerbations.

The use of the proposed preparation is no impediment to drivers.

Hydrazide of diphenylphosphinylacetic acid of the formula:

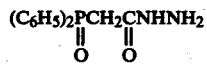

is a generally known compound which can be produced by interacting ethyl ester of diphenylphosphenylacetic acid with hydrazine hydrate.

Consider an example of producing the proposed preparation 0.296 g of ethyl ether of diphenylphosphinylacetic acid is placed in a half-liter flask provided with a thermometer and a condenser set for distillation. 157.1 g of hydrazine hydrate is added, and the reaction mixture is heated at a temperature of 120° C.; the heating is accompanied by distilling the alcohol during 1.5 to 2 hours. Upon the end of the distillation, the temperature is raised to 150° C., and hydrazine hydrate is removed. When the contents of the distillation flask start to crystallize, the reaction mixture is cooled to 100° C., and the rest of hydrazine hydrate is removed under vacuum at a residual pressure of 10 to 15 mm of mercury. The contents of the flask are cooled and recrystallized with the use 390 ml of ethyl alcohol. This results in 236 g of a white crystalline product having a melting point of 159° to 161° C. The yield is 85 percent of the theoretical. The percentage of the preparation's basic components is as follows: P, 11.28; 11.35; N, 10.14; 10.17; $C_{14}H_{15}O_2N_2P$. Hence: P,11.31; and N, 10.22 percent.

Hydrazide of diphenylphosphinylacetic acid is a bitter-tasting odorless white crystalline powder. It is soluble in water (1:100), alcohol and chloroform, but insoluble in benzene and ether.

The proposed compound is mixed with starch and calcium stearate and pressed into pills having a weight of 0.30 g and an active principle content of about 83 percent (0.25 g).

What is claimed is:

1. Method of providing a vegetropic and antiepileptic effective a patient requiring the same, which comprises administering to such patient a vegetropic and antiepileptic effective amount of the hydrazide of diphenylphosphinylacetic acid of the formula:

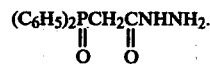

2. Method according to claim 1 wherein the administration is oral.

3. Method of providing an antiserotonin effect in a patient requiring such, which comprises administering to said patient for antiserotonin purposes an antiserotonin effective amount of the hydrazide of diphenylphosphinylacetic acid.

* * * * *